(12) United States Patent
Johannsen et al.

(10) Patent No.: US 11,773,050 B2
(45) Date of Patent: *Oct. 3, 2023

(54) METHOD AND APPARATUS FOR PRODUCING BIOFUEL IN AN OSCILLATING FLOW PRODUCTION LINE UNDER SUPERCRITICAL FLUID CONDITIONS

(71) Applicant: Circlia Nordic ApS, Aarhus (DK)

(72) Inventors: Ib Johannsen, Risskov (DK); Anders Peter Stubkjær Adamsen, Hobro (DK); Bjørn Sjøgren Kilsgaard, Aarhus (DK); Viktor Milkevych, Randers (DK)

(73) Assignee: Circlia Nordic ApS, Hasel (DK)

( * ) Notice: Subject to any disclaimer, the term of this patent is extended or adjusted under 35 U.S.C. 154(b) by 7 days.

This patent is subject to a terminal disclaimer.

(21) Appl. No.: 17/203,796

(22) Filed: Mar. 17, 2021

(65) Prior Publication Data
US 2021/0347720 A1    Nov. 11, 2021

Related U.S. Application Data

(63) Continuation of application No. 15/324,914, filed as application No. PCT/DK2015/050209 on Jul. 9, 2015, now Pat. No. 11,001,550.

(30) Foreign Application Priority Data

Jul. 11, 2014    (DK) .......................... PA201470437

(51) Int. Cl.
*B01J 3/00*    (2006.01)
*B01J 3/02*    (2006.01)
(Continued)

(52) U.S. Cl.
CPC ............... *C07C 67/08* (2013.01); *B01J 3/008* (2013.01); *B01J 3/02* (2013.01); *B01J 3/042* (2013.01);
(Continued)

(58) Field of Classification Search
None
See application file for complete search history.

(56) References Cited

U.S. PATENT DOCUMENTS 4,271,007 A * 6/1981 Souhrada ............. B01J 19/0026
366/124
5,658,610 A * 8/1997 Bergman ................. B01J 3/008
426/599
(Continued)

FOREIGN PATENT DOCUMENTS

WO    WO-2012095176 A1 * 7/2012 .......... B01F 11/0071

OTHER PUBLICATIONS

Harvey A, et al. "Process intensification of biodiesel productionn using a continuous osillatory flow reactor," Journal of Chemical Tecnology and Biotechnology, vol. 78, Jan. 1, 2003, pp. 338-341, John Wiley & Sons, Hoboken, NJ, USA.
(Continued)

*Primary Examiner* — Jennifer A Leung
(74) *Attorney, Agent, or Firm* — Casad & Associates ApS

(57) ABSTRACT

The invention discloses a method for producing bio-fuel (BF) from a high-viscosity biomass using thermo-chemical conversion of the biomass in a production line (10) with pumping means (PM), heating means (HM) and cooling means (CM). The method has the steps of 1) operating the pumping means, the heating means and the cooling means so that the production line is under supercritical fluid conditions (SCF) to induce biomass conversion in a conversion zone (CZ) within the production line, and 2) operating the
(Continued)

pumping means so that at least part of the production line is in an oscillatory flow (OF) mode. The invention is advantageous for providing an improved method for producing biofuel from a high-viscosity biomass. This is performed by an advantageous combination of two operating modes: supercritical fluid (SCF) conditions and oscillatory flow (OF).

7 Claims, 11 Drawing Sheets

(51) Int. Cl.
| | |
|---|---|
| B01J 4/00 | (2006.01) |
| B01J 19/24 | (2006.01) |
| C10G 1/00 | (2006.01) |
| C07C 67/08 | (2006.01) |
| C10L 1/02 | (2006.01) |
| C10L 8/00 | (2006.01) |
| B01J 3/04 | (2006.01) |
| C10G 3/00 | (2006.01) |
| B01J 19/00 | (2006.01) |
| C07C 37/00 | (2006.01) |
| C07C 51/00 | (2006.01) |
| C07D 307/34 | (2006.01) |

(52) U.S. Cl.
CPC .............. *B01J 4/007* (2013.01); *B01J 4/008* (2013.01); *B01J 19/0013* (2013.01); *B01J 19/241* (2013.01); *B01J 19/2415* (2013.01); *C07C 37/004* (2013.01); *C07C 51/00* (2013.01); *C07D 307/34* (2013.01); *C10G 1/00* (2013.01); *C10G 3/40* (2013.01); *C10L 1/02* (2013.01); *C10L 1/026* (2013.01); *C10L 8/00* (2013.01); *B01J 2219/00087* (2013.01); *B01J 2219/00159* (2013.01); *B01J 2219/00162* (2013.01); *B01J 2219/00164* (2013.01); *C10G 2300/1011* (2013.01); *C10L 2200/0476* (2013.01); *C10L 2270/026* (2013.01); *C10L 2290/06* (2013.01); *Y02E 50/10* (2013.01); *Y02P 20/54* (2015.11)

(56) References Cited

U.S. PATENT DOCUMENTS

| 11,001,550 B2* | 5/2021 | Johannsen | ............... C10G 3/40 |
| 2009/0059718 A1* | 3/2009 | Tessien | ................. B01J 19/008 |
| | | | 366/267 |
| 2012/0171090 A1* | 7/2012 | Chang | .................... B01J 19/243 |
| | | | 422/641 |
| 2015/0273430 A1* | 10/2015 | Roelands | ............. B01J 19/1831 |
| | | | 366/341 |
| 2021/0237014 A1* | 8/2021 | Johannsen | ............... C10G 3/40 |
| 2021/0237026 A1* | 8/2021 | Johannsen | ............... C07C 51/00 |
| 2021/0347720 A1* | 11/2021 | Johannsen | ................. C10L 8/00 |

OTHER PUBLICATIONS

Zheng M, et al. "Biodiesel reation screening using oscillatory flow meso reactors," Process Safety and Environmental Protection, vol. 85, No. 5, Jan. 1, 2007, pp. 365-371, Institution of Chemical Engineers, Rugby, GB.

Azhari, T., et al. "Preliminary design of oscillatory flow biodiesel reactor for continuous biodielse production from Jatropha triglycerides," Journal of Engineering Science and Technology, vol. 3, Jan. 1, 2008, pp. 138-145, School of Engineering, Taylor's University College, Subang Jaya, Malaysia.

Poljansek, I. et al., "Influence of mass transfer and kinetics on biodiesel production process," Chapter 19 from Mass Transfer in Multiphase Systems, pp. 433-458, Feb. 2011, InTech, Rijeka, Croatia.

Gzil, Piotr "Communication pursuant to Article 94(3) EPC," pp. 1-3, Aug. 2021, European Patent Office, Rijswijk, Netherlands.

* cited by examiner

METHOD AND APPARATUS FOR PRODUCING BIOFUEL IN AN OSCILLATING FLOW PRODUCTION LINE UNDER SUPERCRITICAL FLUID CONDITIONS

CROSS-REFERENCE TO RELATED APPLICATIONS

This application is a continuation of U.S. patent application No. 15/324914 filed on Jan. 9, 2017 which is the US national stage entry of PCT application No. PCT/DK2015/050209 filed on Jul. 9, 2015, which claims priority to Danish patent application No. PA 2014 70437, filed on Jul. 11, 2014, the disclosures of each of which is hereby expressly incorporated by reference in entirety.

FIELD OF THE INVENTION

The present invention relates to a method for operating an oscillating flow production line in a production system, e.g. a hydrothermal reactor, to produce bio-fuel, or bio-based chemicals, from biomass, such as lignin material from straw. The invention also relates to a corresponding production line or production system.

BACKGROUND OF THE INVENTION

Bio-fuel and bio-based chemicals production is an area of intense research and development because of the world-wide transition from fossil fuel to climate neutral fuels, such as biofuels produced from biomass, e.g. as waste product from agricultural production. Methods using super-critical fluid conditions (SCF) for biofuel production by thermo-chemical conversion have been known for some time. Notice that thermo-chemical conversion is sometimes referred to as hydrothermal conversion or hydrothermal liquefaction, the conversion mainly being controlled by the availability of additional chemicals and catalysts, and conversion temperature as well as pressure. Super-critical fluid operations conditions (SCF) are advantageous because of the fast reaction kinetics, high conversion degrees, low viscosity, and strongly reduced need for additional chemicals and catalysts. The disadvantage is the need for high temperature and high pressure, and the corresponding complexity and cost associated with such operation conditions of the reactor. For a recent review of this technical area, the skilled reader is referred to Wen et al. in *Progress in Natural Science* 19 (2009), 273-284.

Many SCF reactors are operating in continuous mode with a production line i.e. not in a batch mode because of the need for large-scale production of biofuel. A traditional way of scaling up a continuous flow production is by using a tubular reactor in which a pump is feeding one end of a relatively long tube, typically consisting of a preheating zone, a heated reactor zone and a cooling zone. The reaction time may then be influenced, among other factors, by the flow rate and the tube length. If long reaction time is needed either a very long tube, or a very low flow rate is needed. However, both of these solutions are in most cases not feasible due to on one hand large costs and pressure drops, and on the other hand low heat transfer efficiency, risk of sedimentation/clogging and low productivity. Especially in the case of bio-based slurries, it is well known that they have a Non-Newtonian (thixotropic) behaviour, and that their viscosity can increase several orders of magnitude when the shear rate is approaching zero. Thus, at low flow rates their viscosity will be very high and thus the pressure drop, pumping resistance and inverse heat transfer will be very high. This will be a large challenge especially in the parts of the process where the temperature is relatively low, i.e. in transport and heat exchanger zones.

Hence, an improved method for operating a production system for producing biofuel from biomass would be advantageous, and in particular a more efficient and/or reliable method would be advantageous.

OBJECT OF THE INVENTION

It is a further object of the present invention to provide an alternative to the prior art.

In particular, it may be seen as an object of the present invention to provide a method for operating a production system for producing biofuel and bio-based chemicals from biomass that solves the above mentioned problems of the prior art with reaction time, low production, clogging, and/or limited scalability of the production line.

SUMMARY OF THE INVENTION

Thus, the above described object and several other objects are intended to be obtained in a first aspect of the invention by providing a method for producing bio-fuel (BF), or other bio-based chemicals, from biomass (BM), preferably a high-viscosity biomass, in a continuous flow production line, preferably using thermo-chemical conversion of the biomass, the production line comprising:

pumping means (PM) capable of pumping the biomass through the production line under a controlled pressure and flow, heating means (HM) in thermal contact with a first part of the production line for controlling the temperature in the production line, and cooling means (CM) in thermal contact with a second part of the production line for cooling the biomass under conversion, the method comprising:

operating the pumping means, the heating means and the cooling means so that, at least part of, the production line is under supercritical fluid conditions (SCF), optionally at near-supercritical fluid conditions, so as to induce biomass conversion in a conversion zone (CZ) within the production line, and operating the pumping means so that, at least part of, the production line is in an oscillatory flow (OF) mode, wherein a local oscillatory flow rate of the biomass under conversion is superimposed on the average flow rate through the production line.

The invention is particularly, but not exclusively, advantageous for providing a method for producing biofuel from a high-viscosity biomass, e.g. from lingo-cellulosic biomass, high cellulose containing material, lignin containing biomass, manure, food production by-products, and waste water sludge. This is essentially performed by an advantageous combination of two kinds of different operating modes; supercritical fluid (SCF) conditions and oscillatory flow (OF). The present invention may be capable of solving problems in this technical field with reaction time, clogging of reactors, and/or scalability of production to large reactors. The oscillating flow enables that the flow in, at least part of, the production line increases resulting in a lower viscosity. Lower viscosity enables higher heat transfer from the heating means to the biomass, which, in turn, improves the effectiveness of the production line. The lower viscosity of the biomass also makes it possible to operate the production line at lower average flow rate, which may therefore raise the overall reaction time in the production line, while at the same time yielding a high conversion. The supercritical fluid conditions in combination with the oscillatory flow thus facilitate faster and/or improved conversion of the biomass.

The method and production line according to the present invention is particularly suited for yielding biofuel, e.g. biodiesel, for use in later energy production. The invention is however also suited for yielding other products, broadly defined bio-based chemical product from biomass, such as phenols, other aromatic compounds, substituted furanes, lactates, acrylates and oligomeric versions of the afore mentioned.

In context of the present invention, a supercritical fluid may be defined as a substance at temperature and pressure above its critical point where distinct and separate liquid and gas phase do not exist. Super-critical (near) fluids are fluids existing above the critical point in the pressure-temperature range. Near critical fluids may be fluids above 60%, preferably above 70%, or more preferably above 80% of the absolute temperature and/or pressure of the critical point. As the skilled reader will recognise, the dual properties of the liquid and the gas phases may then be exploited for enhanced biofuel production, or other bio-based chemical products. Preferably, the temperature in the conversion zone may be at least 500 K, preferably at least T 600 K, more preferably at least 650 K. Additionally or alternatively, the pressure in the conversion zone may be at least 13 MPa, preferably at least 17 MPa, more preferably at least 22 MPa. The critical temperature and pressure of water is approximately 647K and 220 bar, for ethanol it is approximately 514K og 60 Bar, and for methanol it is approximately 513K and 80 bar, respectively. For mixtures of fluids, a reasonable estimate of the critical temperature and pressure can often be found by a weighted average between the molecular amounts of the fluid components. For information on supercritical fluids, the skilled reader is referred to Brunner, G. (2010). "Applications of Supercritical Fluids". *Annual Review of Chemical and Biomolecular Engineering* 1: 321-342 and references cited therein.

Oscillatory flow may be defined by the resulting flow having an average flow rate determined by the feed rate into the production line, and a local flow rate superimposed on the average flow rate determined by the oscillating pressure of the pumping means, preferably the oscillatory pressure being provided by dedicated oscillatory flow inducing means. Notice that in several prior art applications of oscillatory flow, e.g. in oscillatory flow reactors (OFR), the tubes of the reactor comprises equally spaced orifice plate baffles that separates the reactor into effectively separate 'stirred tanks' with possible positive impact on the mixing and hence conversion yields. However, the present invention is not intended, though not excluded, for having such internal baffles as they may typically negatively influence ease of manufacturing and later cleaning and maintenance. The oscillatory flow may be characterized by the various features including, but not limited to, stroke length of the piston, or equivalent, generating the oscillatory flow, frequency, resulting shear rate, the average flow rate (from little to high flow flow) in combination with the local flow rate, etc.

Within the context of the present invention, it is to be expected that the oscillatory flow superimposed on the average flow through the production line may be damped from the imposing site or point down through the production line, i.e. in some embodiments only a part of the production line may be said to be in oscillatory flow (OF) mode if the damping completely or almost completely dampens the oscillatory flow out. In particular, it is contemplated that the part of the production line being under (near) supercritical fluid conditions (SCF) may significantly dampen the oscillatory flow due to the combined gas and liquid-like properties of the supercritical fluid facilitating such damping.

Within the context of the present invention, it is further to be understood that biomass may include materials and products of biological origin, typically available in large quantities/bulk from living or recently living organisms. Within the context of the present invention, it is to be understood that a production line is an extended processing system where the entering bio-mass is conveyed by suitable transportation means through a number of process steps, where at each step one or more processes occur, e.g. pressurizing, heating, conversion of bio-mass, cooling, depressurizing, etc., and eventually the resulting biofuel, or other bio-based chemicals, is conveyed out of the production line. The term production line may be synonymous with a production system for carrying out the method according to the invention.

By the term 'continuous flow', it is particularly to be understood that the bio-mass flows with a non-zero flow rate through the production line, preferably all the time or most of the time during operation of the production line. Thus, continuous flow may be considered, at least for some purposes, as the opposite of a batch-like process.

Within the context of the present invention, the thermochemical conversion includes, but is not limited to, hydrothermal conversion of biomass. Hydrothermal conversion of biomass may, without being bound to any specific theory, be defined as chemical processes performed at elevated temperatures in the presence of a liquid phase, such as water or other polar solvents that will convert biomass into lower molecular weight components, such as biofuels and other chemical mixtures.

Within the context of the present invention, shear thinning fluids may include, but not being limited to, thixotropic and pseudoplastic fluids, i.e. fluids that will exhibit shear thinning either depending on shear rate alone (pseudoplastic) or shear rate and time (thixotropic) A special type of shear thinning also relevant for biomass slurries is Bingham plastic behaviour in which the material behave solid-like up to a certain shear stress. It should be mentioned that biomass typically has highly shear thinning properties, which may significantly influence the viscosity and thereby pressure drop and heat conductivity through the biomass i.e. changing the shear rate may cause changes in viscosity by several orders of magnitude. For further details on the rheology properties of bio-mass, the skilled reader is for example referred to *Rheology measurements of a biomass slurry: an inter-laboratory study* by Jonathan J. Stickel et al. in Rheol Acta (2009) 48:1005-1015, which is hereby incorporated by reference in its entirety.

In an advantageous embodiment, wherein the production line may comprise oscillatory flow inducing means (OFIM) in fluid contact with the production line, the OFIM preferably being distinct from the pumping means. Preferably, the oscillatory flow inducing means may comprise:
- one or more positive displacement pumps, such as membrane/diaphragm based pumps, or piston based pumps,
- one or more velocity pumps, such as centrifugal type pumps,
- one or more impulse pumps,
- one or more gravity pumps,
- one or more steam pump, and/or one or more valveless pumps
for inducing oscillatory flow in the production line.

Optionally, when operating the production line in an oscillatory flow (OF) mode it may comprise that the local flow has an alternating direction of flow with an oscillatory frequency (f_osc) through at least part of the production line, preferably in at least said first part 1 of the production line, and/or in at least part of the conversion zone (CZ). In some embodiments, the entire production line may be operated in a OF mode.

In one embodiment, the oscillatory flow inducing means (OFIM) may be positioned in fluid contact with the production line at, or near, the said first part of the production line and operated for inducing an oscillatory flow in at least part of the production line, preferably in at least said first part of the production line for increasing the heat transfer, and/or in at least part of the conversion zone (CZ) for increasing the conversion efficiency.

In another alternative or combined embodiment, the oscillatory flow inducing means (OFIM) may be positioned in fluid contact with the production line at, or near, the said second part of the production line and operated for inducing an oscillatory flow, preferably in at least said first part and/or said second part of production line and/or in at least in part of the conversion zone (CZ) for increasing the conversion efficiency.

In some embodiments, the temperature, the pressure, and the flow rate may be controlled so as to subject the biomass to a sufficient shear stress for obtaining shear thinning properties, or near shear thinning properties, of the biomass at least in part of production line, preferably in at least said first part of production line and/or in at least in part of the conversion zone (CZ), In some embodiments, the entire production line may be operated so that the biomass has shear thinning properties, or near shear thinning properties.

Preferably, the conversion zone of the production line under supercritical fluid conditions (SCF) may be positioned in the production line between the said first part and the said second part of the production line to improve heating and cooling effectiveness.

Optionally, the production line, at least in the conversion zone (CZ), may have a tubular (internal) structure, preferably with a substantially unchanged inner diameter in the conversion zone (CZ), in order to lower clogging, ease maintenance and cleaning, and/or for simplifying the manufacturing process.

In some embodiment, the heating means may be supplied with heat from said cooling means via heat exchanging means for increased efficiency. Particularly, the production line in said first part and/or second part have a tubular structure, the heating exchanging means may comprise a entity made of a heat conduction material, preferably manufactured in a metal or a metal alloy, surrounding the tubular structures in both the first and/or the second part for conducting the heat from the second part to the first part in the production line. Furthermore, the heating exchanging means may comprise a fluid cooling medium for conducting the heat from the second part to the first part in the production line via fluid flow in the heat exchanging means, the fluid flow in the heat exchanging means preferably being arranged in a counter-flow relative to the biomass under conversion in the production line for further increased efficiency.

Typically, the production line may comprise a depressurizing unit at an outlet for the resulting biofuel (BF), or bio-based chemical, from the production line, by which the product is released in a semi-continuous, or continuous, manner from the production line and depressurized from the supercritical pressure in the production line. Advantageously, the oscillatory flow inducing means (OFIM) may then be operably connected to the depressurizing unit, the pressure energy released during depressurizing being, at least partly, conveyed to the pumping means (PM) and/or the oscillatory flow inducing means (OFIM) for increased pump efficiency.

In one embodiment, one, or more, hydraulic accumulators may be arranged as a pressure storage reservoir for absorbing pressure energy from the depressurizing unit for temporally storing pressure energy, and the one, or more, hydraulic accumulators being arranged for conveying, at least partly, the stored pressure energy to the oscillatory flow induction means (OFIM) thereby reusing the stored pressure energy resulting in improved cost efficiency of the production line. Advantageously, the biomass feed into the production line may be selected from the group consisting of: lignin-based material, lignocellulosic biomass, high cellulose containing material, lignin containing biomass, manure, food production by-products, and waste water sludge. Some biomass type may have an initial viscosity being at least 0.01, preferably at least 0.1, more preferably at least 1 PaS. The skilled person in rheology will appreciate that viscosity is not easy to measure because it can depend on a number of factors involved in the measurement itself, in particular because biomass typically behaves like a non-Newtonian fluid. Accordingly, the initial viscosities listed above may depend on the measurement method as it will be understood and therefore apply for several measurement methods useful for biomass viscosity.

In a second aspect, the invention further relates to a production line for producing biofuel, or other bio-based chemicals, from biomass in a continuous flow, preferably using thermo-chemical conversion of the biomass, the production line comprising
    pumping means (PM) capable of pumping the biomass through the production line under a controlled pressure and flow,
    heating means (HM) in thermal contact with a first part of the production line for controlling the temperature in the production line, and
    cooling means (CM) in thermal contact with a second part of the production line for cooling the biomass under conversion,
wherein the pumping means, the heating means and the cooling means are arranged for being operated so that, at least part of, the production line is under supercritical fluid conditions (SCF), optionally at near-supercritical fluid conditions, so as to induce biomass conversion in a conversion zone (CZ) within the production line, and
wherein the pumping means are arranged for being operating so that, at least part of, the production line is in an oscillatory flow (OF) mode, wherein a local oscillatory flow rate of the biomass under conversion is superimposed on the average flow rate through the production line.

In a third aspect, the invention relates to a computer program product being adapted to enable a computer system comprising at least one computer having data storage means in connection therewith to control a production line according to the first and/or second aspect of the invention.

This aspect of the invention is particularly, but not exclusively, advantageous in that the present invention may be accomplished by a computer program product enabling a computer system to carry out the operations of the production line of the first and/or second aspect of the invention when down- or uploaded into the computer system. Such a computer program product may be provided on any kind of computer readable medium, or through a network.

In a preferred embodiment, the computer program product may be further arranged for receiving inputs related to at least temperature, pressure and flow rate through the production line, and based on said input further being arranged for outputting an apparent value of viscosity for the biomass entering the production line, the computer program product further enabling adjustment (either manually, semi-automatic or automatic) of the production line based on said apparent value of viscosity for the biomass. This is particular advantageous because it facilitates real-time measurement of viscosity of the incoming biomass which is quite important for operating the production line at optimum or near optimum performance.

The first, second and third aspect of the present invention may each be combined with any of the other aspects. These and other aspects of the invention will be apparent from and elucidated with reference to the embodiments described hereinafter.

BRIEF DESCRIPTION OF THE FIGURES

The invention will now be described in more detail with regard to the accompanying figures. The figures show one way of implementing the present invention and are not to be construed as being limiting to other possible embodiments falling within the scope of the attached claim set.

DETAILED DESCRIPTION OF AN EMBODIMENT

Figure 1:
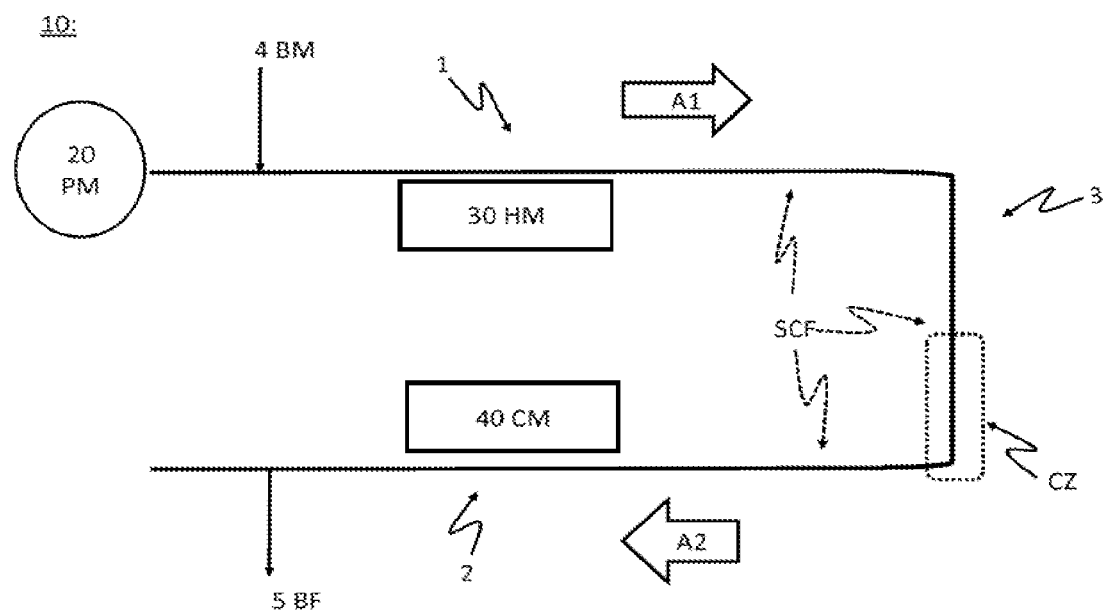
FIG. 1 is a schematic drawing of the production line according to the present invention.

FIG. 1 is a schematic drawing of the production line 10 according to the present invention. The invention also relates to a method for producing bio-fuel BF 5 (as indicated by arrow in the lower part of the production line) or other bio-based chemicals, from biomass BM 4 entering the production line (as also indicated with arrow in the upper part of the Figure). The biomass is preferably a high-viscosity biomass, e.g. with a viscosity of 0.1 PaS or higher. The production line 10 is advantageously operated in a continuous flow. The production line 10 preferably uses thermo-chemical conversion of the biomass. The conversion may optionally be assisted by added chemicals, e.g. catalysts, acids or bases, etc. Appropriate solvents may also be added, e.g. water or other polar solvents. The production line comprises pumping means 20 PM, e.g. one or more pumps, capable of pumping the biomass 4 through the production line under a controlled pressure, P, and flow. The production line 10 also comprises heating means HM in thermal contact with a first part 1 of the production line for controlling the temperature, T, in the production line. Additionally, the production line comprises cooling means CM 40 in thermal contact with a second part 2 of the production line 10 for cooling the biomass under conversion.

The method according to the invention particularly comprises operating the pumping means 20, the heating means 30 and the cooling means 40 so that, at least part of, the production line 10 is under supercritical fluid conditions (SCF), optionally at near-supercritical fluid conditions, so as to induce biomass conversion in a conversion zone CZ within the production line. In FIG. 1, the conversion zone is schematically shown as being smaller than the part of the production line being operated at SCF (or near SCF) conditions, but in other embodiments the conversion zone and the part of the production line under SCF conditions may be the same (i.e. overlapping and coinciding), or substantially the same.

The method according to the invention further comprises operating the pumping means PM 20 so that, at least part of, the production line 10 is in an oscillatory flow OF mode, wherein a local oscillatory flow rate of the biomass under conversion is superimposed on the average flow rate through the production line 10.

Thus, in some embodiments the whole production line 10 is operated in an oscillatory flow OF mode, including the supercritical fluid SCF zone and the conversion zone CZ. In other embodiments, only parts of the production line 10 is operated in an oscillatory flow OF mode, for example the part of the production line 10 from the pumping means PM 20 inducing the oscillatory flow and parts of the conversion zone CZ. In some embodiments, the oscillatory flow mode may extend into parts of the supercritical fluid SCF zone but not covering the conversion zone CZ due to the damping taking place of the oscillatory flow in the supercritical fluid SCF zone.

In FIG. 1, the flow direction through the production line 10 is schematically indicated by arrows A1 and A2, though it should be remembered that the imposed oscillatory flow OF may cause the instantaneous flow to be shortly in the opposite direction in the production line 10, though the average flow direction will be as indicated.

Figure 8:
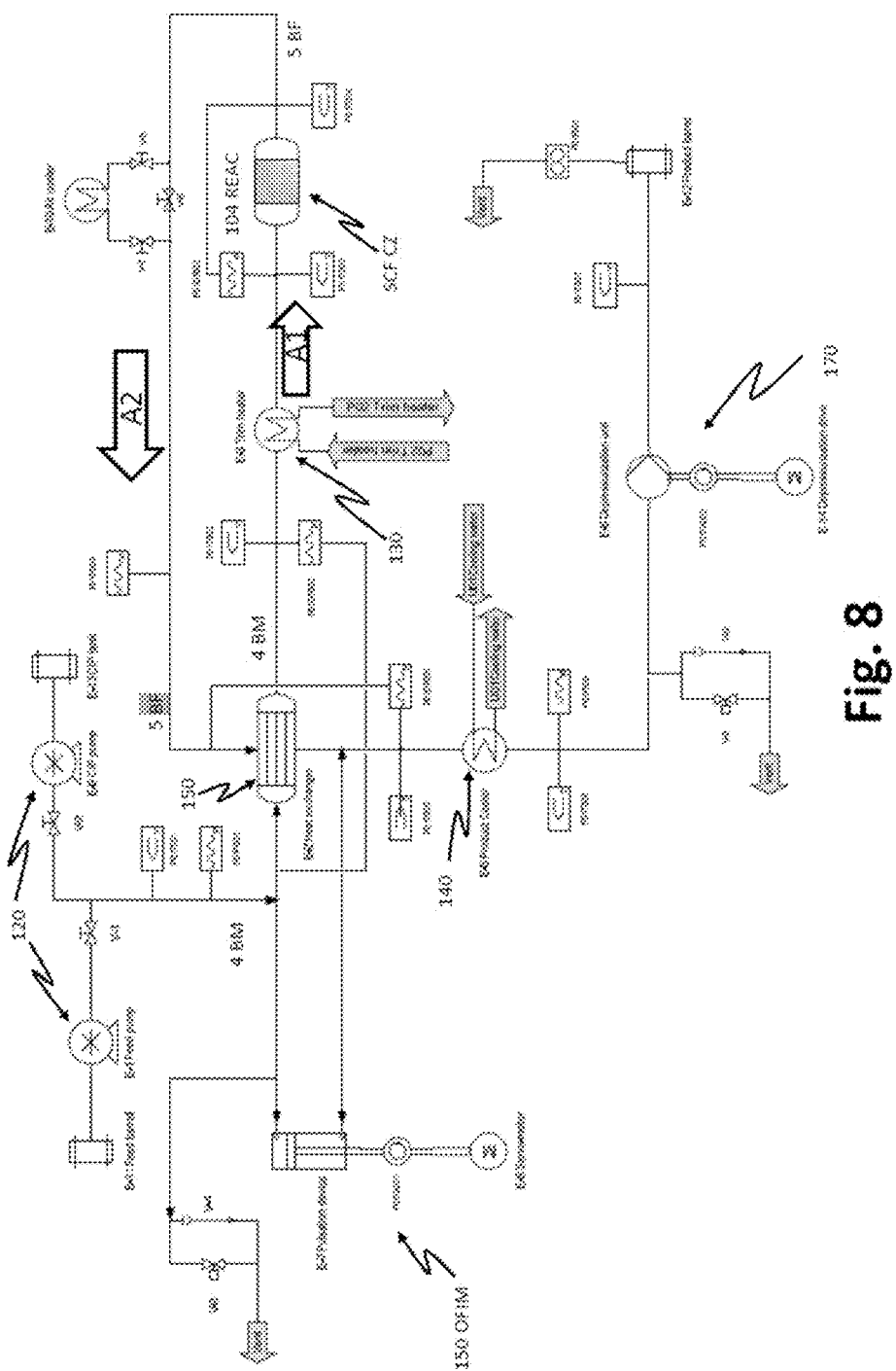
FIG. 8 is a more detailed schematic drawing of a production line according to the present invention.

The production line 10 shown is schematically indicated in FIG. 1, but the skilled person is referred to e.g. FIG. 8 for a more detailed embodiment of a production line 10. It may be mentioned that various steps, including but not limited to, such as pre-treatment, preheating, separation, purification, chemical upgrading incl. hydrogenation, are also foreseen within the context of the present invention for producing biofuel, or other bio-based chemicals, from biomass as it will be appreciated by the skilled person once the general teaching and principle of the present invention has been acknowledged.

Within the context of the present invention, the pumping means PM 20 may comprise electrically driven, hydraulically driven, and/or pneumatically driven pumps. The pumps may be positive displacement pumps, e.g. piston based pumps, or velocity pumps, e.g. centrifugal type pumps. The pumping means may include extruders for feeding biomass under pressure, or eccentric screw pumps. Alternative pumping means include impulse pumps, gravity pumps, steam pumps, and valveless pumps.

Figure 2:
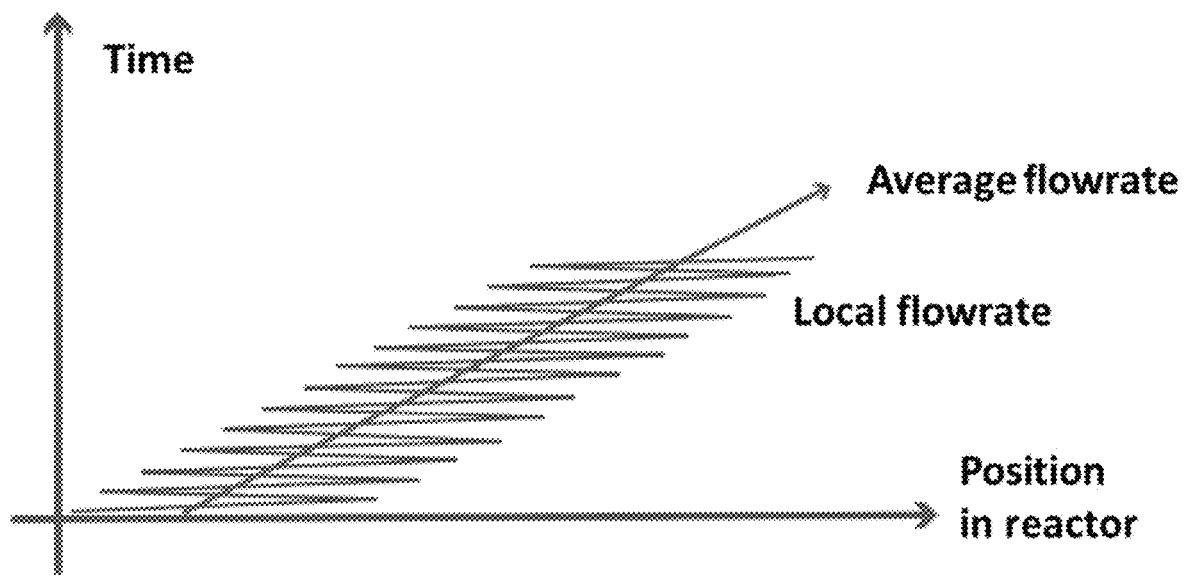
FIG. 2 is a schematic graph of the time versus the position for illustrating oscillatory flow.

FIG. 2 is a schematic graph of the time (vertical axis) versus the position (horizontal axis, 'reactor' being synonymous with the conversion zone, CZ) for illustrating some aspects of the oscillatory flow OF according to the present invention. As seen in the graph, the average flow rate is constant but the local flow rate is oscillating. The position, in the example shown in FIG. 2, is going back and forth i.e. local flow rate is alternating direction between forward and backwards (position being larger and smaller, respectively) thereby increasing the reaction time in the production line 10. The average flow direction is, however, positive i.e. the flow through the production line will take place as indicated by arrows A1 and A2 in FIG. 1.

According to the invention further the pumping means PM 20 are operated so that, at least part of, the production line 10 is in an oscillatory flow OF mode, the local oscillatory flow rate of the biomass under conversion is superimposed on the average flow rate through the production line as shown in the graph of FIG. 2. In advantageous embodiments, the local flow rate and average flow rate may, at least to some extent, be adjusted independently of each other enabling even better yield of the product i.e. biofuel. When operating the production line 10 in an oscillatory flow OF mode, the local flow may thus have an alternating direction of flow through the production line 10 at least in part of the conversion zone CZ. The alternating direction may change with an oscillatory frequency, f_osc, set by the operator of the production line and/or set automatically by control means (not shown) of the production line. In some embodiments, the oscillatory flow may have just a forward direction.

Figure 3:
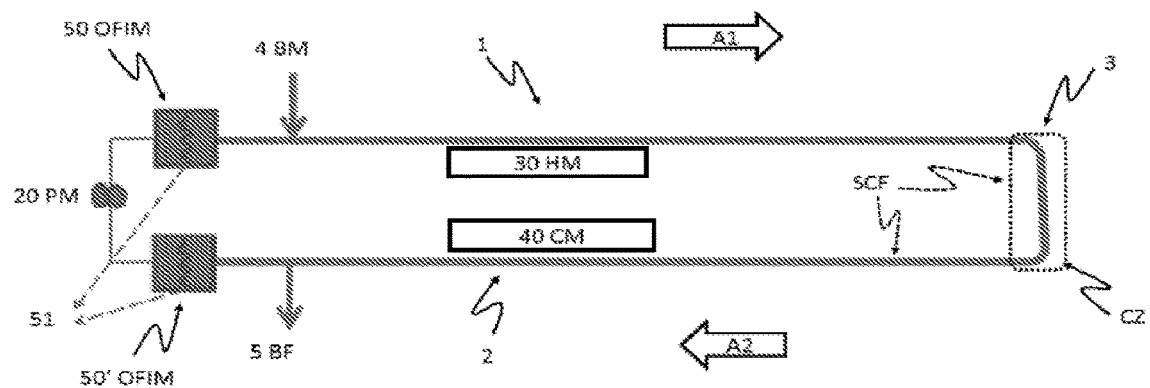
FIG. 3 is another schematic drawing of the production line with oscillatory flow inducing means according to the present invention.

FIG. 3 is another schematic drawing of the production line with oscillatory flow inducing means OFIM 50 and 50' according to the present invention but otherwise similar to FIG. 1. Thus, the production line 10 comprises an oscillatory flow inducing means, e.g. two membrane-based pumps with membranes 51 schematically indicated. The pumps 50 and 50' are in fluid contact with the production line, and the oscillatory flow inducing means are different from said pumping means 20, the pumping means 20 providing the average flow through the production line 10. The oscillatory flow inducing means 50 and 50' may thus comprise one, or more, membrane(s) 51 as shown for inducing the oscillatory flow through the production line. In the embodiment shown, the membrane-based pumps 50 and 50' are provided both at the biomass 4 inlet and near the bio-fuel 5 outlet, respectively, as schematically shown. In this way, the oscillatory flow can better be maintained through the production line by such an up-stream and down-stream oscillatory flow provider.

The oscillatory flow inducing means 50 is positioned in fluid contact with the production line 10 at, or near, the first part 1 of the production line and operated for inducing an oscillatory flow to at least in part of the conversion zone CZ. Similarly, the oscillatory flow inducing means 50' is positioned in fluid contact with the production line at, or near, the second part 2 of the production line 10 and operated for inducing an oscillatory flow back stream through the production line 10 back to at least part of the conversion zone CZ. In embodiments of the invention, only one of the OFIM pumps may be used, i.e. either pump 50 or pump 50'.

As seen in FIGS. 1 and 3, the conversion zone CZ of the production line under (near) supercritical fluid conditions SCF is positioned at part 3 of the production line between the first part 1 and the second 2 part of the production line where the heating and cooling, respectively, take place.

Within the context of the present invention, the oscillatory flow inducing means may comprise electrically driven, hydraulically driven, and/or pneumatically driven pumps. The pumps may be positive displacement pumps, e.g. piston based pumps or membrane based pumps, or velocity pumps, e.g. centrifugal type pumps. The oscillatory flow inducing means of FIG. 3 are membrane-based pumps, below various other types of pumps are illustrated, though the skilled person will readily understand that several other types of pumps may be applied within the context of the present invention once the general teaching and principle of the invention has been understood.

Figure 4A:
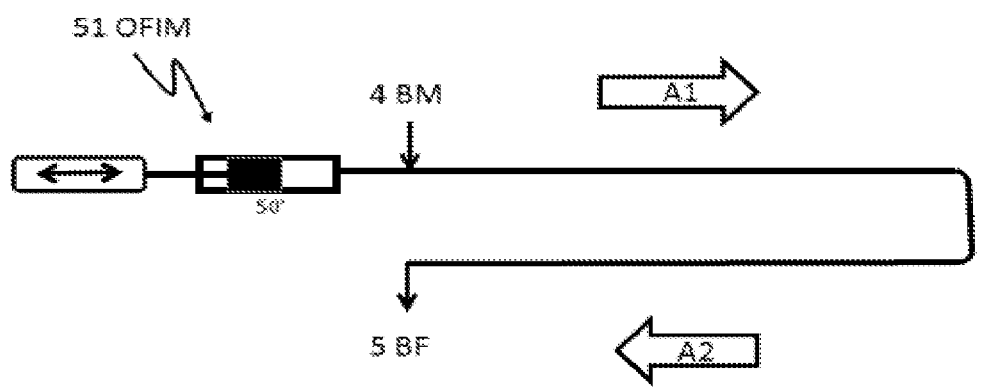
FIGS. 4A, 4B and 4C show other schematic drawings of the production line with oscillatory flow inducing means of the piston type according to the present invention.
Figure 4B:
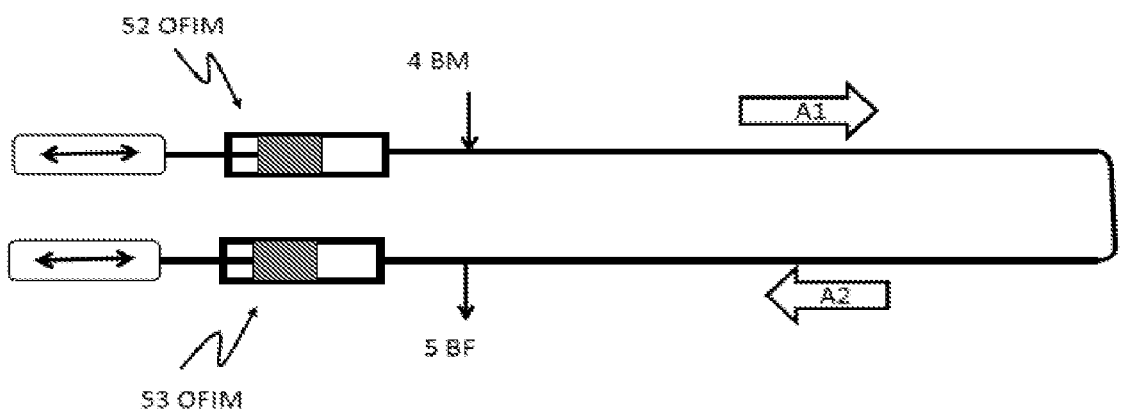

FIGS. 4A and 4B show other schematic drawings of the production line with oscillatory flow inducing means OFIM of the piston type according to the present invention. These means for providing oscillatory flow may in some embodiments also be applied for providing the average flow through the production line 10.

FIG. 4A schematically shows a production line 10 with a single piston-based pump OFIM 51 i.e. a positive displacement pump being positioned upstream relative to the inlet of biomass 4 BM.

FIG. 4B schematically shows a production line 10 with two piston-based pumps OFIM 52 and 53 being positioned upstream and downstream, respectively, relative to the inlet of biomass 4 BM. This is technically similar to the double membrane based embodiment of FIG. 3.

Figure 4C:
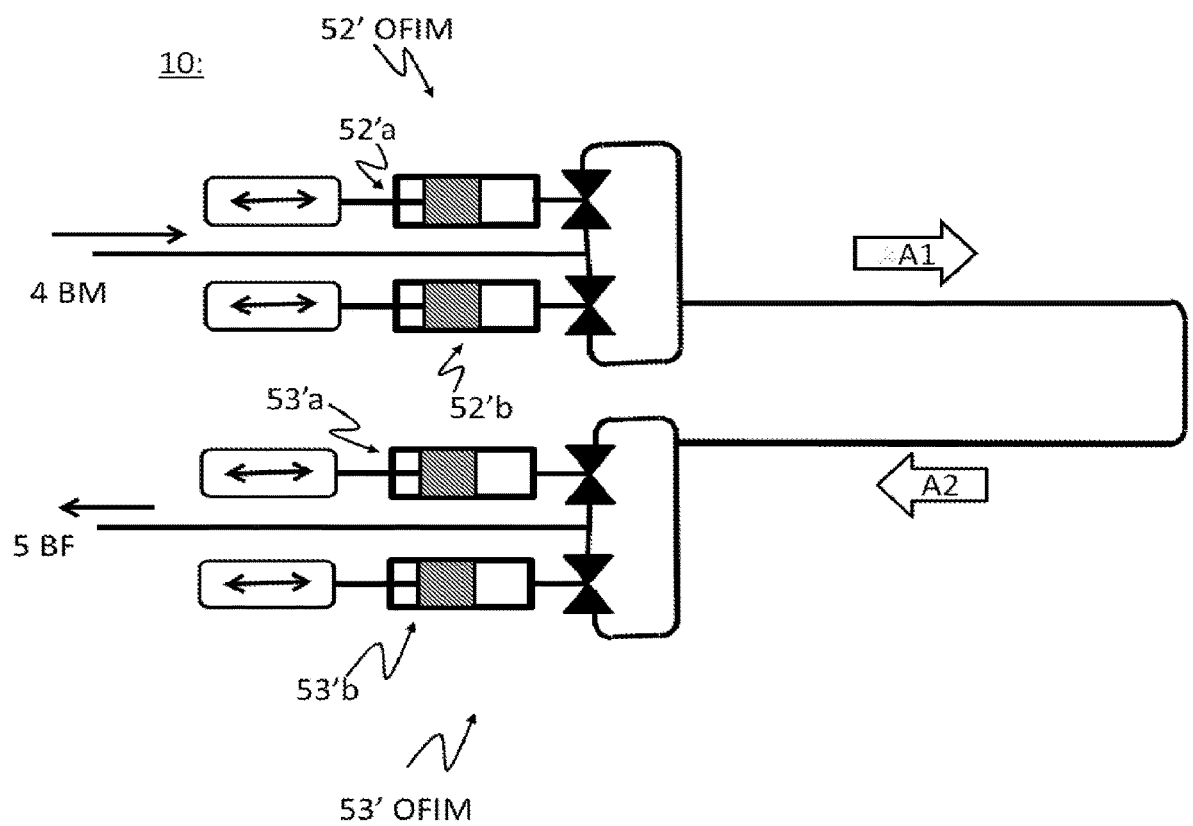

FIG. 4C schematically shows another production line 10 with two double piston-based pumps OFIM 52' and 53' being positioned upstream and downstream, respectively, relative to the inlet of biomass 4 BM. As further development of the embodiment of FIG. 4B, the pumps OFIM 52' and 53' each have a double piston based functionality with the respective set of pistons generally working in counter-phase to neighbouring piston to create the most optimum oscillatory flow through the production line 10. In such a setup the double pumps will be able to act as a combined feeding and oscillation pump and a combined depressurization and oscillation pump, respectively. The associated actuators are shown next to each piston with a double-arrow as will be understood by the skilled person in hydraulics. Thus, the first set of pistons 52'*a* and 52'*b* may work in counter-phase to each other, their corresponding working pressure being controlled by the associated valves as schematically indicated in FIG. 4C, and similarly for the other set of pistons 53'*a* and 53'*a'*.

Figure 5:
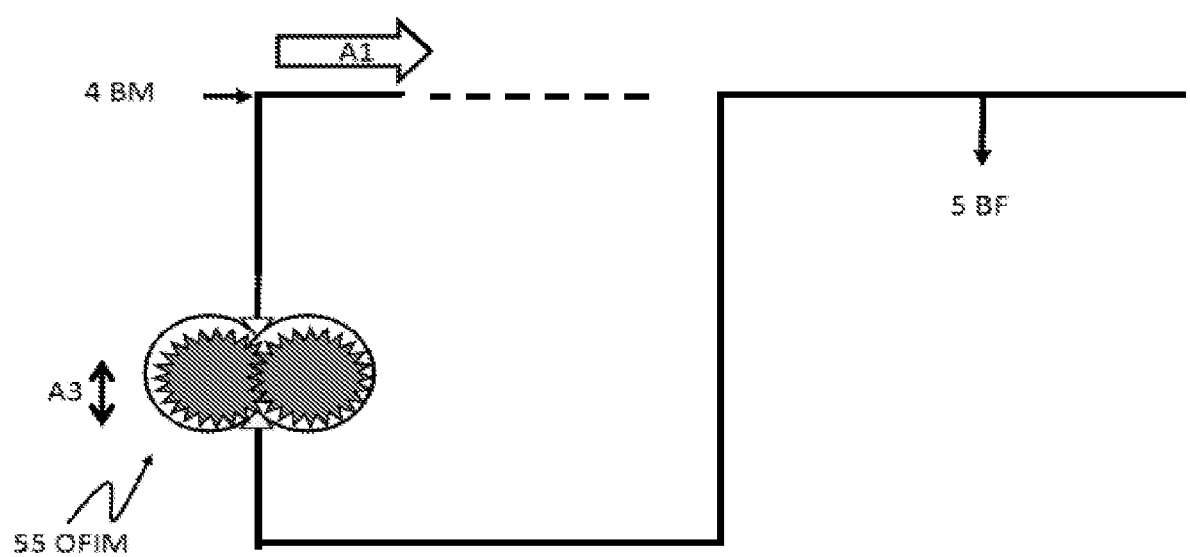
FIG. 5 shows yet another schematic drawings of part of the production line with oscillatory flow inducing means comprising a reverse gear pump according to the present invention.

FIG. 5 shows yet another schematic drawing of part of the production line 10 with oscillatory flow inducing means OFIM 55 comprising a reverse gear pump according to the present invention. Technically, a single entity can thereby produce both oscillatory flow both upstream and downstream relative to the average flow direction, the average flow direction being schematically indicated by arrow A1. The dotted line after the arrow A1 indicates that only part of the production line 10 is shown here. When implementing this embodiment, the skilled person should consider the issue of backflow i.e. whether, and to what degree, the produced bio-fuel on the downstream side of the pump 55 is allowed to flow back into the starting part of the production line. If sufficient piping distances are implemented into the production line this may be solved.

Figure 6:
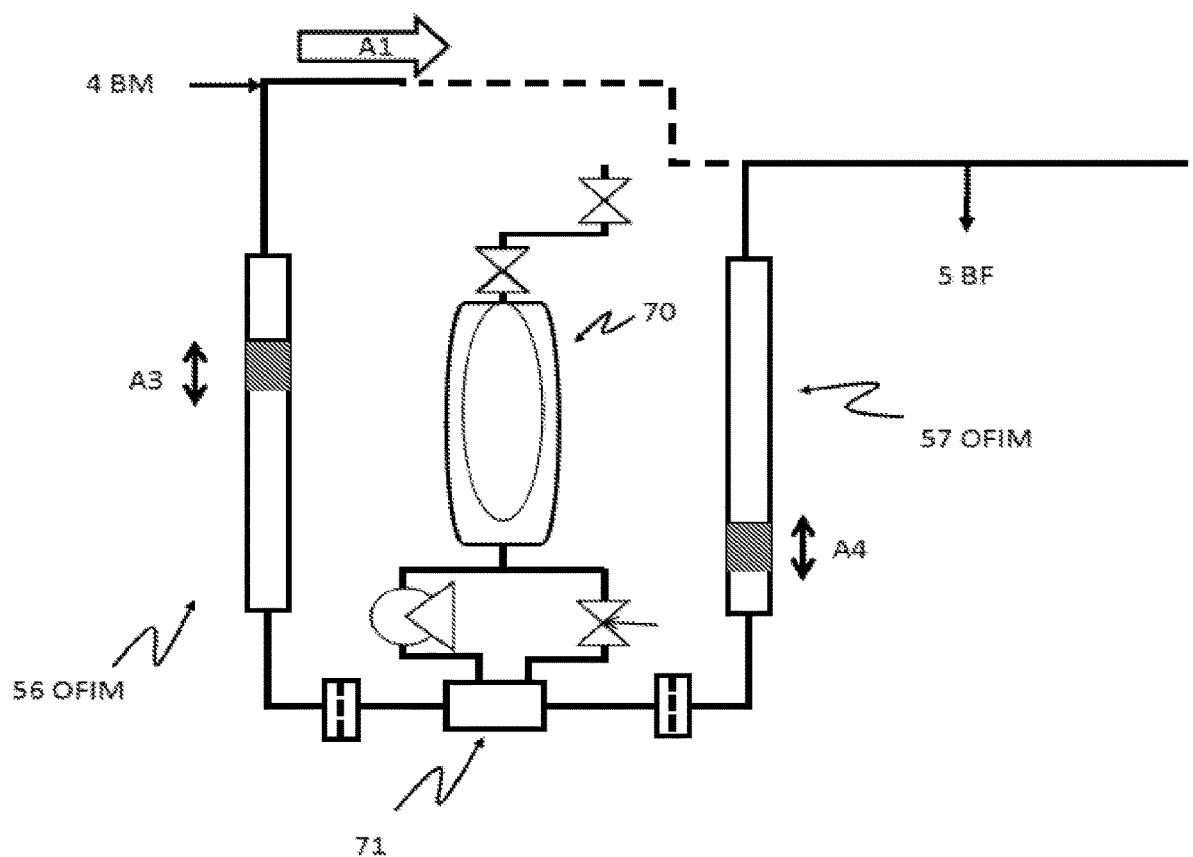
FIG. 6 shows yet another schematic drawing of part of the production line with oscillatory flow inducing means comprising a hydraulic accumulator according to the present invention.

FIG. 6 shows yet another schematic drawing of part of the production line 10 with oscillatory flow inducing means OFIM 56 and 57 comprising a hydraulic accumulator 70 according to the present invention. OFIM 56 and 57 may be implemented as so-called media separators known in hydraulics, commercial vendors of such equipment being for example HYDAC, Parker, HiP (High Pressure Equipment Company), etc. This embodiment has the advantage that the driving force for the oscillatory movement only has to overcome the pressure difference between the hydraulic accumulator and the process line. The pressure difference may be in the range of 5 to 100 bar depending on the needed driving force to overcome the friction in the flow pattern of the system. The described use of hydraulic accumulators strongly reduces the energy consumption and pump investments costs. Possible accumulators include, but is not limited to, separator-less accumulators, gas charged accumulators (piston or bladder), spring-loaded piston accumulators, weight loaded accumulators, and diaphragm accumulators.

The production line comprises a depressurizing unit and take off unit (not shown in FIG. 6 but see FIG. 7) at an outlet for the product from the production line, by which the product is released in a semi-continuous, or continuous, manner from the production line and depressurized from the high pressure in the production line 10. The depressurising unit may comprise the piston OFIM 57 on the downstream side by absorbing at least part of the pressure via the piston. The pressure energy may subsequently be temporally stored in accumulator 70. Thus, the depressurizing unit is operably connected to a hydraulic accumulator arranged as a pressure storage reservoir for absorbing pressure energy and temporally storing the pressure energy, the hydraulic accumulator 70 being further arranged for releasing the stored pressure energy to the oscillatory flow inducing means OFIM 56 via hydraulic circuit means, in particular the switch valve 71, e.g. 4/2 switch valve, so as to reuse the hydraulic energy from the production line. Appropriate vents for operating the hydraulic accumulator 70 are also shown in FIG. 6.

Figure 7:
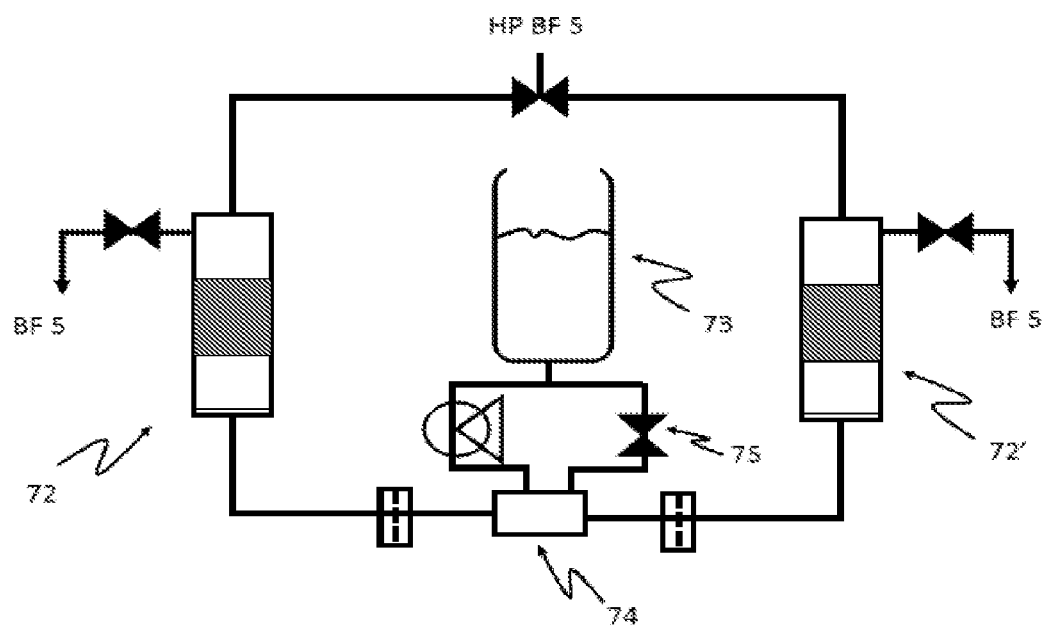
FIG. 7 shows a depressurizing unit according to the present invention.

FIG. 7 shows a depressurizing unit 170 according to the present invention. The bio-fuel BF 5 is initial under a high pressure, as indicated by symbol HP, after being conveyed away from the supercritical fluid SCF pressurized zone. The pistons 72 and 72' absorb at least part of the high pressure in the fluid reservoir tank 73 with an open top connected to the pistons 72 and 72' by appropriate fluid connecting means, in particular a distributor valve 74, e.g. a 4/2 four way valve, and a constant flow valve 75. The tank 73 could alternatively be closed with a valve to the surroundings. The combined action of the tank 73 and the pistons 72 and 72' is to function as a damper as it will be appreciated. The product BF 5 is conveyed from the depressurization unit 170 to the product tank that also can act as a gas separation unit, allowing the gaseous byproducts to be analyzed.

The depressurizing unit may alternatively, or additionally, comprise one or more of the following depressurizing means; needle valves, capillary tubes etc. In particular, various pumps and combination thereof may be used, such as an electrically driven, hydraulically driven, and/or pneumatically driven pump. The pumps may be positive displacement pumps, e.g. piston based pumps, membrane (diaphragm) based pumps, gear pumps, progressing cavity pump, impeller based pumps, rotary lobe pumps, rotary vane pumps, or velocity pumps, e.g. centrifugal type pumps. Especially, they may have double action.

FIG. 8 is a more detailed schematic drawing of a production line 10 according to the present invention. FIG. 8 is a so-called Piping, Instrumentation and Design (PID) diagram, well-known in hydraulics, of the production line 10. Various pressure gauges, valves, safety valves, gas separator, product tanks, CIP system, and sensors etc. are shown in FIG. 8 but will not be separately explained apart from certain elements of the invention.

Pumping means 120 are capable of pumping the biomass 4 BM through the production line under a controlled pressure and flow. Initially, the biomass BM enters a heat exchanger 150 (from the left in FIG. 8). On the primary side (not shown) of the heat exchanger the biomass will then be heated from hot biofuel 5 BF from the secondary side (shown), the biofuel entering from the top of the heat exchanger as seen in FIG. 8. Thus, some heating will take place.

Secondly, heating means HM 130 in thermal contact with the production line 10 facilitate control of the temperature and thereby resulting in further heating of the biomass. The heated biomass then enters the reactor part 104 REAC of the production line 10 under (near) supercritical fluid condition. In the reactor, the biomass will be converted to biofuel 5 BF. The drawing in FIG. 8 is schematic so the extent of the conversion zone CZ may not be accurate but merely illustrative.

Thus, the production line is operated so that the pumping means 120 and 150, the heating means and the cooling means so that, at least part of, the production line is under supercritical fluid conditions SCF, optionally at near-supercritical fluid conditions, so as to induce biomass conversion in a conversion zone CZ, here reactor 104 REAC, within the production line 10.

Additionally, the production line 10 is operated so that the pumping means 120 and the oscillatory flow inducing means 150 are able to keep, at least at part of, the production line in an oscillatory flow OF mode, wherein a local oscillatory flow rate of the biomass under conversion is superimposed on the average flow rate through the production line 10.

As shown in FIG. 8, there may further be provided cooling means CM 140 in thermal contact with a second part of the production line for further cooling the biofuel BF 5 after leaving the heat exchanger 150. Optionally, the heat extracted from the biofuel 5 BF in cooling means 140 may be re-used in heating means 130.

Suitable heating exchangers 150 and the combined heat exchanger of cooler 140 and heater 130 may include, but is not limited to, tube-by-tube configuration joined in a highly thermally conductive material, a segmented heat exchanger, heat exchanger using a cooling medium, such as oil, salt melting medium, hot water medium, etc., as the skilled person in thermodynamics would readily contemplate for use when designing, implementing and operating a production line for producing biofuel, or other bio-based chemicals, from biomass according to the present invention.

It should be noted that even though the production line 10 shown in FIG. 8 is operated at least partly in an oscillatory flow OF, cf. FIG. 2 and corresponding description thereof above, by carefully controlling the pumping means 120 and the OFIM 150, there is no need for designing the tubes in the production line 10 with baffles to achieve oscillatory flow. On the contrary, it is intended that the pipes or tubes may have essentially the same diameter, at least on parts or sections of the line 10, providing easier design, manufacturing, operating (e.g. no clogging) and/or maintenance, especially cleaning.

It may be mentioned that the depressurizing unit 170 may be functionally connected to the OFIM 150 and the pumping means 120 for optionally re-using the energy in the high pressure product of biofuel BF 5. Particularly, the depressurizing unit 170 can be fluid-wise connected to the OFIM 150 with an additional pressure accumulator for temporally storing the pressure energy, and later reuse the pressure energy for creating oscillatory flow in the production line, as explained in more detail in connection with FIG. 6 above.

Figure 9:
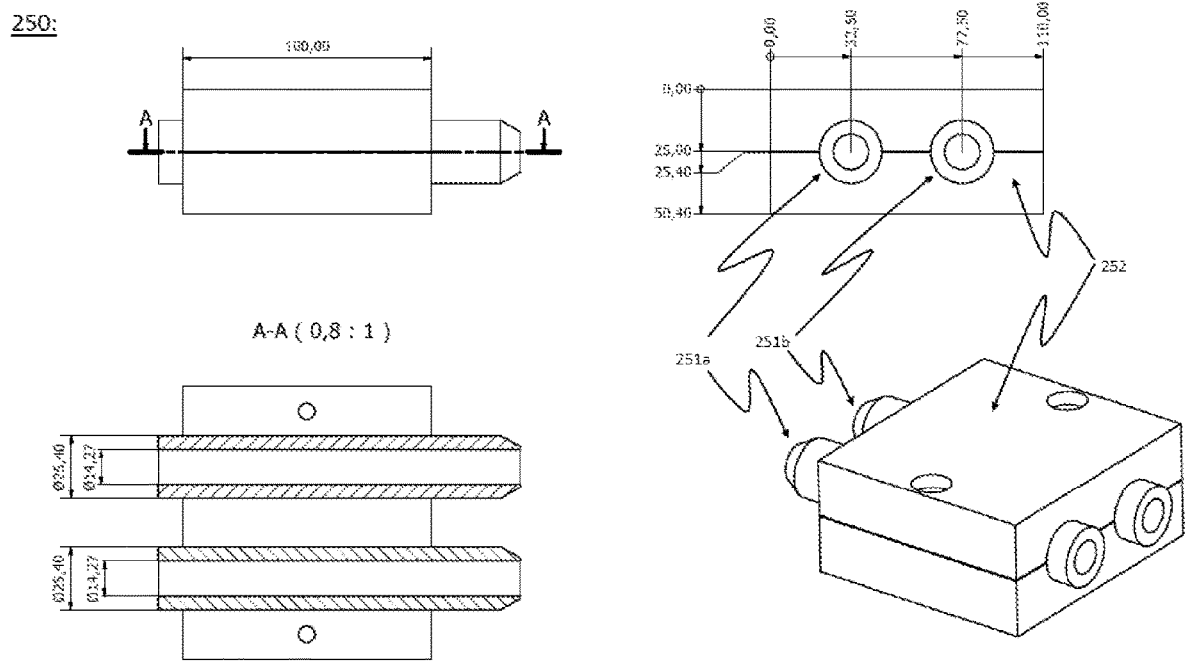
FIG. 9 shows a segment of a heat exchanger according to the present invention.

In a production system for producing bio-fuel etc. according to the present invention as depicted in FIG. 8, the system comprising approximately 124 m of UNS6625 tubing with an inside diameter of 14 mm and where the feed was passed through 24 m of heat exchanger (cold side) tube, 16 m of trimheater tube, 60 m of reactor tube and finally 24 m of heat exchanger (hot side) tube, a number of preliminary experiments were conducted:

The heat transfer was performed through a large number of custom-made heat clamps made out of cast iron, cf. FIG. 9 for an example, to fit the thermal expansion of the tube alloy with a wall to wall distance between the tubes of 26 mm. The preliminary experiments conducted with a reactor temperature of 575 K and pure water as the reference fluid showed that the oscillation reduced the heat loss by 20% in the heat exchanger as compared to the same flow with no oscillation (82% recovery vs 78% for no oscillation).

Furthermore, experiments with fibrous biomass (10% milled Miscantus Gigantus in water containing 1.5% potassium hydroxide) at the above temperature range showed that there was a 10-20% reduction in feed pressure needed to obtain a steady flow of 25 l/hr, indicating a significant reduction in dynamic viscosity of the feed as expected when implementing the present invention.

FIG. 9 shows a segment of a heat exchanger 250 according to the present invention in three planar view and a perspective view. The segment 250 may be manufactured by joining two tube parts 251a and 251b together in solid matrix 252 of relatively good heat conducting material, such as a steel alloy or similar material. A plurality of such segments 250 may form a heat exchanger 150 as shown in FIG. 8. Similarly, the combined heat exchanger of cooling means 140 and heating means 130 may be implemented by such a plurality of segments 250. This has the advantage that at least part of the invention may be manufactured by relatively simple elements keeping cost at a low level. In particularly, it may be noted that the dimensions of the heat segment 250 should be sufficiently strong enough to sustain the production line operating at (near) supercritical pressures and temperatures of the biomass 4 BM. The dimensions shown in FIG. 9 are in millimetres (mm).

Figure 10:
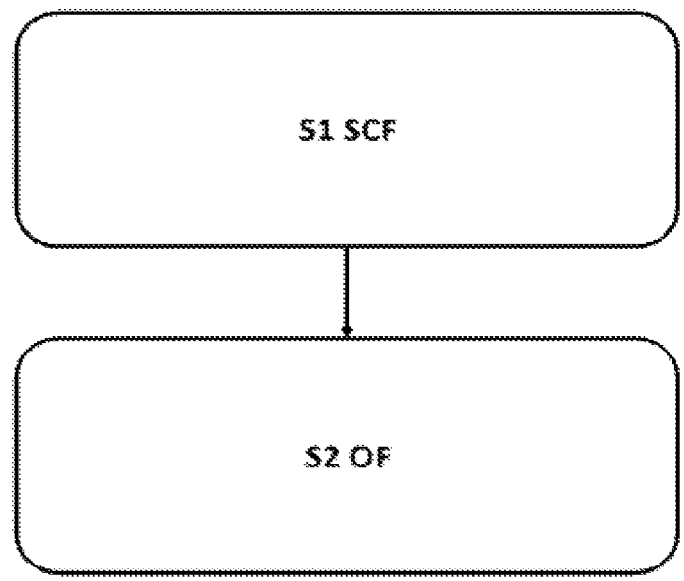
FIG. 10 is a flow-chart of a method according to the invention.

FIG. 10 is a flow-chart of a method according to the invention for producing bio-fuel 5 BF, or other bio-based chemicals, from biomass 4 BM, preferably a high-viscosity biomass, e.g. least 0.1 PaS, in a continuous flow production line 10, preferably using thermo-chemical conversion of the biomass, the production line comprising:

pumping means PM 20 or 120 capable of pumping the biomass through the production line under a controlled pressure and flow, heating means HM 30 or 130 in thermal contact with a first part 1 of the production line for controlling the temperature in the production line, and cooling means CM 40 or 140 in thermal contact with a second part 2 of the production line for cooling the biomass under conversion, the method comprising:

S1 operating the pumping means, the heating means and the cooling means so that, at least part of, the production line is under supercritical fluid conditions SCF, optionally at near-supercritical fluid conditions, so as to induce biomass conversion in a conversion zone CZ, e.g. reactor 104 REAC in FIG. 8, within the production line, and S2 operating the pumping means so that, at least part of, the production line is in an oscillatory flow OF mode, wherein a local oscillatory flow rate of the biomass under conversion is superimposed on the average flow rate through the production line.

In short, the present invention discloses a method for producing bio-fuel BF from a high-viscosity biomass using thermo-chemical conversion of the biomass in a production line 10 with pumping means PM, heating means HM and cooling means CM. The method has the steps of 1) operating the pumping means, the heating means and the cooling means so that the production line is under supercritical fluid conditions SCF to induce biomass conversion in a conversion zone CZ within the production line, and 2) operating the pumping means so that, at least part of, the production line is in an oscillatory flow OF mode. The invention is advantageous for providing an improved method for producing biofuel from a high-viscosity biomass. This is performed by an advantageous combination of two operating modes: supercritical fluid SCF conditions and oscillatory flow OF.

The invention can be implemented by means of hardware, software, firmware or any combination of these. The invention or some of the features thereof can also be implemented as software running on one or more data processors and/or digital signal processors.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A production line for producing biofuel, or other bio-based chemicals, from biomass in a continuous flow, using thermo-chemical conversion of the biomass, comprising:
a biomass inlet,
a tubular reactor,
two double piston based pumps each having associated valves for control of working pressure and each having associated hydraulic actuators situated upstream and downstream relative to the biomass inlet,
heating means (HM) in thermal contact with a first part of the tubular reactor for controlling the temperature in the tubular reactor, and
cooling means (CM) in thermal contact with a second part of the tubular reactor for cooling the biomass under conversion,
wherein the tubular reactor is not equipped with internal baffles that influence mixing.

2. The production line of claim 1 further comprising a heat exchanger including heat clamps made from solid matrixes of heat conducting material that surround the tubular reactor.

3. A method for producing bio-fuel, or other bio-based chemicals, from biomass under continuous flow in the production line of claim 1 comprising:
    operating each of the two double piston-based pumps in a manner such that the two pistons of each double piston-based pump work in counter-phase relative to one another and controlling the corresponding working pressure of the pistons using the associated valves; and
    thermo-chemically converting the biomass in the tubular reactor.

4. A method for producing bio-fuel, or other bio-based chemicals, from biomass under continuous flow in the production line of claim 1 comprising:
    operating the production line in a manner such that the flow in at least part of the tubular reactor oscillates such that local flow has alternating direction between forward and backward, resulting in lower viscosity of the biomass and higher heat transfer; and
    thermo-chemically converting the biomass in the tubular reactor.

5. A method for producing bio-fuel, or other bio-based chemicals, from biomass under continuous flow in the production line of claim 1 comprising:
    maintaining a conversion zone situated between the first part of the tubular reactor in thermal contact with the heating means and the second part of the tubular reactor in thermal contact with the cooling means at a temperature between 500K and 650K; and
    thermo-chemically converting the biomass in the tubular reactor.

6. A method for producing bio-fuel or other bio-based chemicals, from biomass under continuous flow in the production line of claim 1 comprising:
    operating the two double piston-based pumps, the heating means, and the cooling means of the production line in a manner such that a conversion zone (CZ) situated between the first part of the tubular reactor in thermal contact with the heating means and the second part of the tubular reactor in thermal contact with the cooling means is maintained under supercritical or near-supercritical fluid conditions to induce biomass conversion; and
    thermo-chemically converting the biomass in the tubular reactor.

7. A method for producing bio-fuel or other bio-based chemicals, from biomass under continuous flow in the production line of claim 1 comprising:
    thermo-chemically converting the biomass in the tubular reactor in the presence of water or other polar solvents.

* * * * *